United States Patent
Falkvall et al.

(10) Patent No.: US 9,254,357 B2
(45) Date of Patent: *Feb. 9, 2016

(54) CONTAINER, SYSTEM AND METHOD FOR PROVIDING A SOLUTION

(75) Inventors: Thore Falkvall, Helsinborg (SE); Per-Olov Carlsson, Ronneby (SE)

(73) Assignee: METPRO AB, Ronneby (SE)

( * ) Notice: Subject to any disclaimer, the term of this patent is extended or adjusted under 35 U.S.C. 154(b) by 452 days.

This patent is subject to a terminal disclaimer.

(21) Appl. No.: 13/590,056

(22) Filed: Aug. 20, 2012

(65) Prior Publication Data

US 2012/0323209 A1     Dec. 20, 2012

Related U.S. Application Data

(63) Continuation of application No. 12/304,984, filed as application No. PCT/EP2007/055973 on Jun. 15, 2007, now Pat. No. 8,343,129.

(30) Foreign Application Priority Data

Jun. 15, 2006 (SE) ...................... 0601327

(51) Int. Cl.
*A61M 1/16* (2006.01)
*A61J 1/20* (2006.01)
*A61J 1/10* (2006.01)

(52) U.S. Cl.
CPC ............. *A61M 1/1656* (2013.01); *A61J 1/2093* (2013.01); *A61M 1/167* (2014.02); *A61M 1/1666* (2014.02); *A61J 1/10* (2013.01); *A61J 1/1418* (2015.05); *A61J 1/202* (2015.05);

(Continued)

(58) Field of Classification Search
CPC .............. A61J 1/2093; A61J 2205/60; A61J 2001/2024; A61M 1/167; A61M 1/1656
USPC .......... 604/403, 408, 410, 416; 383/38, 210.1
See application file for complete search history.

(56) References Cited

U.S. PATENT DOCUMENTS 5,480,394 A * 1/1996 Ishikawa ........................ 604/327
5,484,431 A * 1/1996 Scharf et al. ................... 604/403

(Continued)

FOREIGN PATENT DOCUMENTS

EP       639364 B1    11/1993
EP       0639354 A2    8/1994

(Continued)

OTHER PUBLICATIONS

Written Opinion and Preliminary Report on Patentability from the International Searching Authority for PCT/EP2007/055973 completed Feb. 7, 2008.

(Continued)

*Primary Examiner* — Leslie Deak
(74) *Attorney, Agent, or Firm* — Knobbe, Martens, Olson & Bear, LLP

(57) ABSTRACT

A container (10) comprising a plurality of compartments (A, B, C) separated by compartment dividers (6), and an inlet connector (3) for receiving a liquid via a connection tube (2). The compartment dividers rupture when a sufficient pressure is applied by a liquid or gas introduced into the container (10) through the inlet connector (3). Some of the compartments comprise powder, which dissolves at the introduction of liquid into the container. A system, process and use in the field of dialysis are also disclosed.

24 Claims, 15 Drawing Sheets

(52) U.S. Cl.
CPC ........... *A61J 1/2024* (2015.05); *A61J 2200/60* (2013.01); *A61J 2200/76* (2013.01); *A61J 2205/10* (2013.01); *A61J 2205/30* (2013.01); *A61J 2205/60* (2013.01); *A61M 2205/3569* (2013.01); *A61M 2205/6018* (2013.01)

(56) References Cited

U.S. PATENT DOCUMENTS

| | | | |
|---|---|---|---|
| 6,007,529 | A | 12/1999 | Gustafsson et al. |
| 6,017,598 | A * | 1/2000 | Kreischer et al. ............ 428/35.4 |
| 6,146,360 | A * | 11/2000 | Rogers et al. ................ 604/151 |
| 6,149,294 | A | 11/2000 | Jonsson et al. |
| 6,645,191 | B1 * | 11/2003 | Knerr et al. .................. 604/410 |
| 6,663,743 | B1 * | 12/2003 | Becker et al. ............... 156/273.7 |
| 7,597,691 | B2 * | 10/2009 | Kawaguchi et al. .......... 604/408 |
| 2002/0138066 | A1 | 9/2002 | Manica et al. |

FOREIGN PATENT DOCUMENTS

| | | |
|---|---|---|
| EP | 0917881 A2 | 5/1999 |
| EP | 1 312 386 A | 5/2003 |
| FR | 2749763 | 12/1997 |
| JP | 07-299134 A | 11/1995 |
| JP | 07299134 | 11/1995 |
| JP | H08-511216 | 11/1996 |
| JP | 2000-504956 | 4/2000 |
| JP | 2005000677 | 1/2005 |
| JP | 2005118445 | 5/2005 |
| WO | WO 9526177 | 10/1995 |
| WO | WO 97/37628 | 10/1997 |
| WO | WO 00/42969 | 7/2000 |
| WO | WO 00/57833 | 10/2000 |
| WO | WO 2004/041149 A1 | 5/2004 |

OTHER PUBLICATIONS

Later Publication of International Search Report for PCT/EP2007/055973 mailed Feb. 7, 2008.

International Preliminary Report on Patentability for PCT/EP2007/055973 completed Nov. 14, 2008.

\* cited by examiner

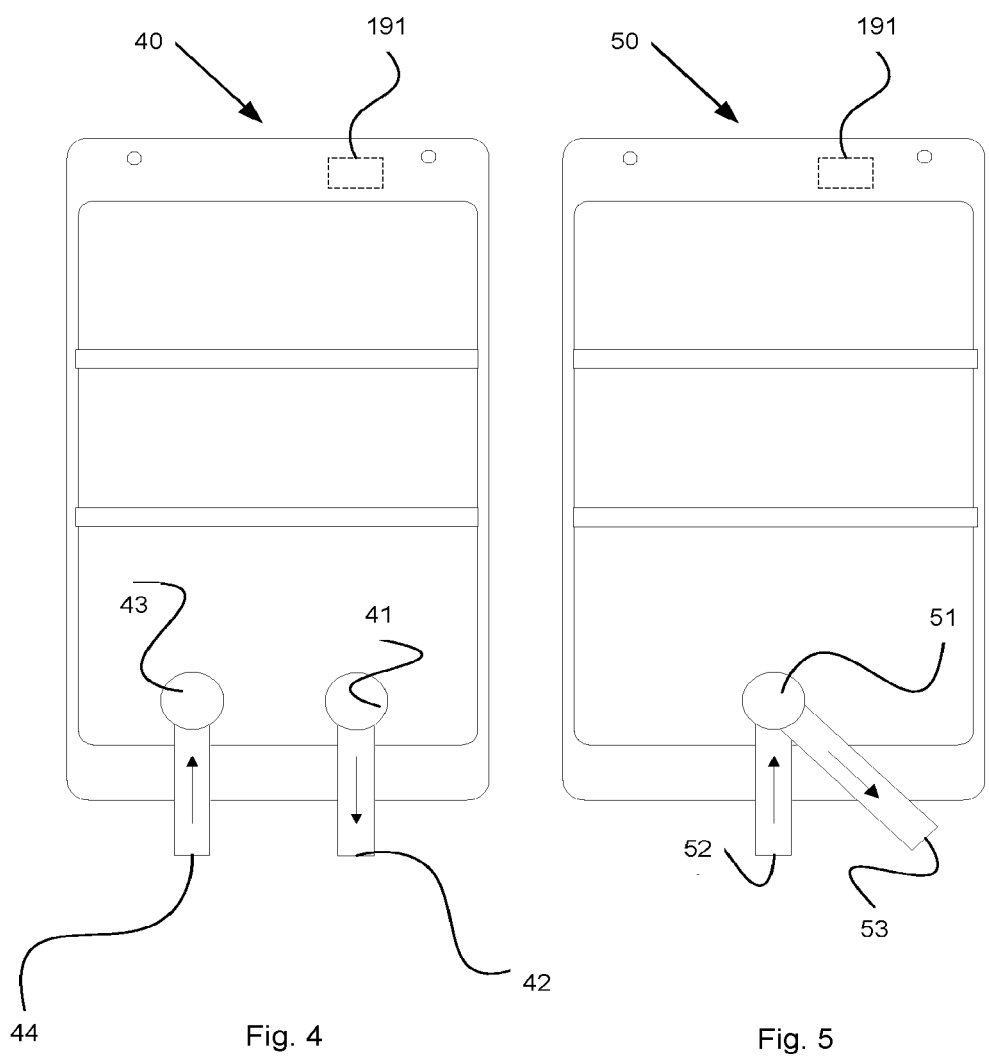

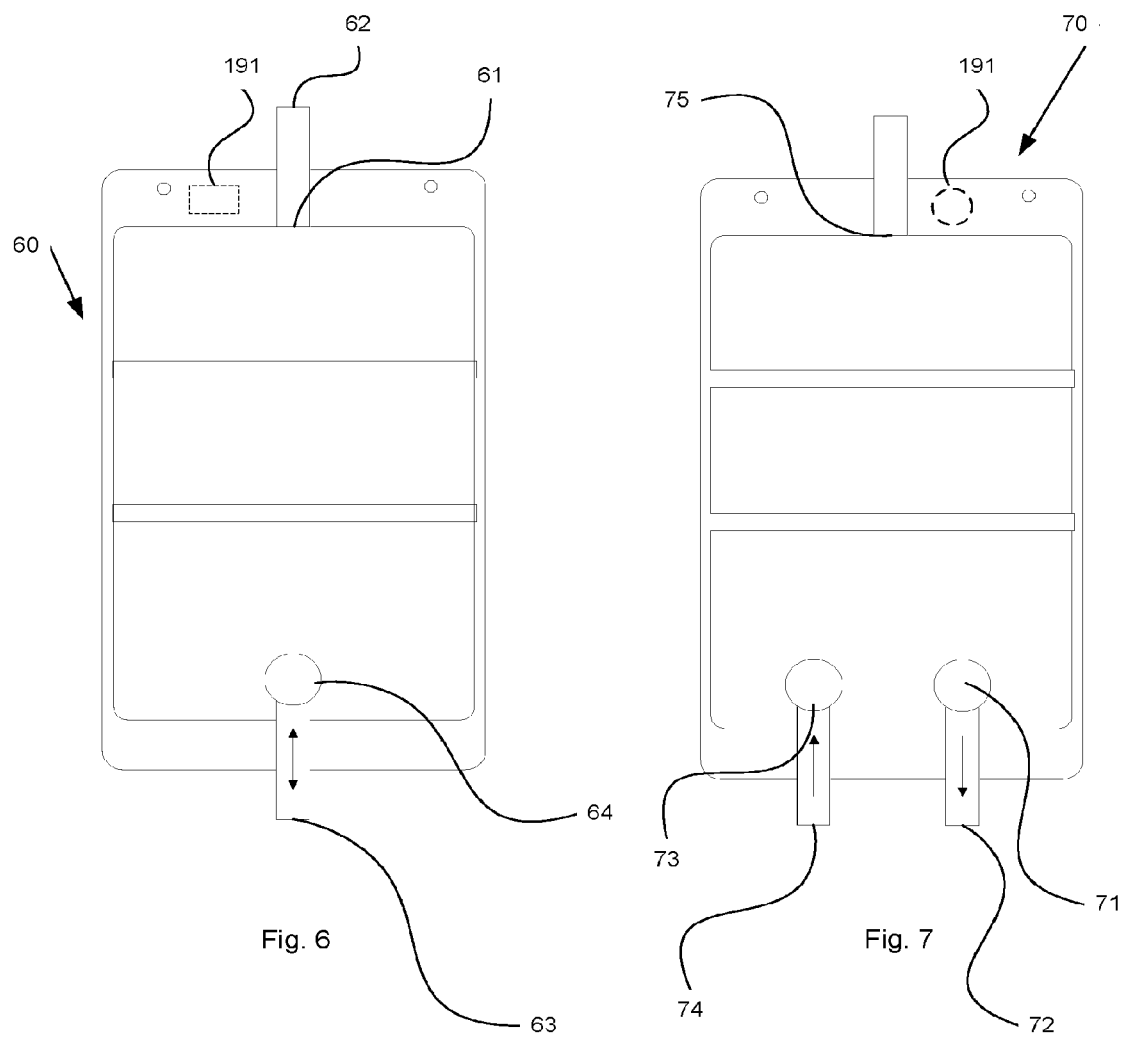

CONTAINER, SYSTEM AND METHOD FOR PROVIDING A SOLUTION

CROSS-REFERENCE TO RELATED APPLICATIONS

This application is a continuation of U.S. application Ser. No. 12/304,984, filed May 29, 2009, which is a national phase of PCT Application No. PCT/EP07/55973, filed Jun. 15, 2007, which claims priority to Swedish Application No. SE 0601327-0, filed Jun. 15, 2006. Each of these applications are hereby incorporated by reference in their entireties.

FIELD OF THE INVENTION

This invention pertains in general to the field of solutions, particularly medical solutions. More particularly the invention relates to a container, a method and a system for providing a medical solution, such as a dialysis solution.

BACKGROUND

U.S. Pat. No. 6,149,294 discloses an apparatus for preparation of fluids intended for medical use from powder. The apparatus comprises a container such that the water and powder can be mixed and a concentrate provided in the container, and a recirculation circuit for recirculation of the water or concentrate solution into the container for further mixing of the water and powder to prepare a concentrate having a predetermined concentration.

This apparatus is able to prepare a ready mixed dialysis solution or replacement solution to be delivered to a dialysis machine performing hemodialysis (HD), hemodiafiltration (HDF) or hemofiltration (HD). The prepared solution may as well be used for other purposes, such as peritoneal dialysis, or as nutritional solution for infusion into the blood of a patient. However, this apparatus comprises several valves and other devices requiring control by a computer. Thus, there is a need for a simpler device for preparing a medical solution.

WO 00/057833 discloses a container for enclosing a medical agent intended to be used in dialysis treatment. The container comprises an electrolyte compartment and a power compartment. Shortly before use, the powder compartment is opened to allow the powder to dissolve in the electrolyte solution in the electrolyte compartment. Further compartments may be provided. The mixed solution is delivered via an outlet tube for subsequent use in for example peritoneal dialysis. The separate compartments are interconnectable by frangible pins or by seals that are breakable by pulling in pull-tabs.

This container requires manual handling in order to connect the different compartments to each other for blending the contents thereof. However, many patients using such medical solutions, for example dialysis patients, have weak muscles, making such pulling in tabs difficult to perform. Thus, there is a need for a container that can be placed in a system, which performs the blending automatically, without the need for intervention by the patient, or with minimal requirement for muscle strength of the patient.

DISCLOSURE OF THE INVENTION

Accordingly, the present invention preferably seeks to mitigate, alleviate or eliminate one or more of the above-identified deficiencies in the art and disadvantages singly or in any combination and solves at least the above-mentioned problems by providing a container, system, process, and use according to the appended patent claims.

According to an aspect of the invention, there is provided a container for enclosing a medical agent, comprising: at least one compartment (A, B, C) comprising the medical agent; an inlet connector for connection to the compartment; at least one separator for separating the at least one compartment from the inlet connector characterized in that the separator is configured to open when a pressure is applied through the inlet connector.

According to another aspect of the invention, there is provided a system for providing a medical solution. The system comprises at least one container comprising an inlet connector for receiving a fluid in a compartment therein, a fluid pump connected to the inlet connector by means of an inlet tube for providing liquid, such as water, from a liquid source (105) to the at least one container a first valve (95) provided between the liquid pump and the inlet connector, which is normally opened, a second valve, which is normally closed, provided between the inlet connector and a solution supply reservoir, such that in use the medical solution is prepared by mixing a contents of the at least one container with the liquid from the liquid source.

According to yet another aspect of the invention, there is provided a method for providing a medical solution. The method comprises introducing a first water volume into a container, according to any of claims 1-20, from a water source via a water pump and via a first valve, providing a pressure by the water pump for opening a first of the at least one compartment dividers, stopping the water pump when the pressure is provided, re-circulating the contents of the container by means of a re-circulation pump with the introduced first sufficient volume of water, thus providing a mixed medical solution, and communicating the mixed medical solution to a solution supply reservoir.

According to another aspect of the invention, there is provided a method for emptying a system according to any one of the claims 20-32. The method comprises: changing direction of the water pump into backward pumping mode, changing direction of the first valve and the second valve into backward flow mode, emptying the system of fluid by pumping the fluid into a drain.

According to another aspect of the invention, there is provided a use of the container according to any one of claims 1 to claim 13 in peritoneal dialysis treatment, such as Continues Ambulatory Peritoneal Dialysis or Continuous Cycling Peritoneal Dialysis, Hemofiltration batch and Hemodiafiltration batch.

According to yet another aspect of the invention, there is provided a use of the container according to claims 1-19 in dialysis treatment, such as Hemodialysis, Hemofiltration online and Hemodiafiltration online.

BRIEF DESCRIPTION OF THE DRAWINGS

These and other aspects, features and advantages of which the invention is capable of will be apparent and elucidated from the following description of embodiments of the present invention, reference being made to the accompanying drawings, in which FIGS. 1 to 8 are schematic illustrations of containers in the form of bags according to different embodiments;

DETAILED DESCRIPTION OF EMBODIMENTS

The following description focuses on embodiments of the present invention applicable to a dialysis system and in particular to the preparation of a dialysis liquid or dialysis concentrates of different concentrations using powder concentrates. However, it will be appreciated that the invention is not limited to this application but may be applied to many other liquid mixing and solution providing systems. Thus, medical solutions prepared by the embodiments described below can be used in dialysis treatments, as concentrate solutions or ready-made solutions for dialysis, as infusion solutions, such as Ringer's lactate, as nutrition solutions, as replacement solutions, as plasma expander solutions, etc.

Figure 1:
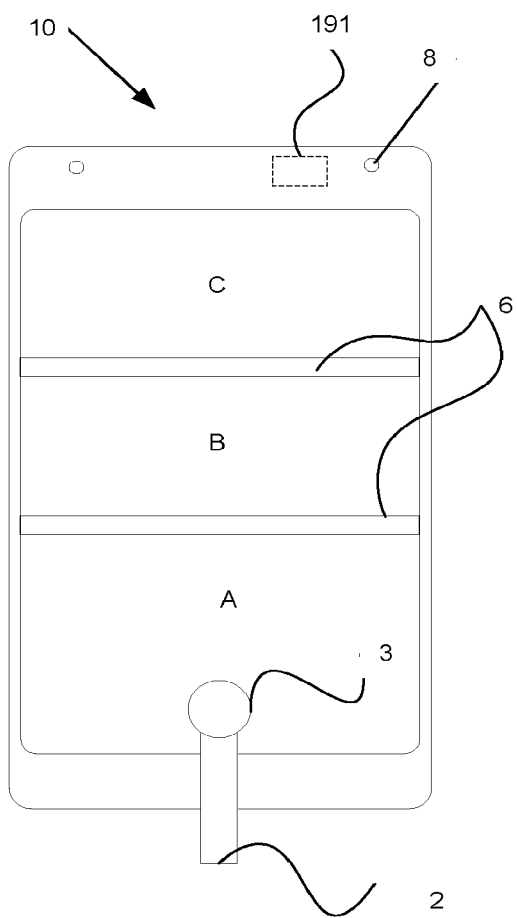

FIG. 1 discloses a container, such as a bag, 10 comprising two compartment dividers 6, which divides the bag 10 into three compartments A, B, and C. The compartments A-C may contain powder or liquids in amounts suitable for providing a solution, such as a dialysis, by dissolving the powder in liquid and by mixing the contents of the compartments A-C. The bag 10 may optionally be attached to a hanger using e.g. a hole 8 or a terminal strip, etc.

The bag 10 is provided with an inlet connector 3, connected to an inlet tube 2 for introducing a fluid, such as water or a gas, into compartment A of the bag. When the fluid enters the bag 10 through the inlet connector 3, the compartment dividers 6 are arranged to break or rupture in order to connect the compartments to each other as further described below.

The first compartment divider 6' between compartments A and B will break when the fluid pressure inside the compartment A connected to the inlet 3 exceeds a predetermined first pressure. Then, the first compartment A is connected to the second compartment B and the contents thereof may blend with each other and mix.

When the first compartment divider 6' opens, the fluid pressure may drop due to the increase in volume of compartment A together with compartment B. By continued introduction of additional fluid into the bag, the fluid pressure therein increases to a predetermined second pressure so that the second compartment divider 6' between compartments B and C will open and provide communication between compartment B and compartment C. Thus, a second blending and mixing of the contents of compartment C and the contents of compartments A and B is provided.

The first and second predetermined pressures are mainly based on the design of the bag and the respective compartment divider. In some embodiments the first and second predetermined pressure is identical, however due to the design of the bag, in terms of stiffness in the used material and the design of the respective compartment divider, the predetermined pressure may vary between different bags and between the first and second predetermined pressure within a bag. For example a predetermined pressure for a compartment divider may be 1-2 bar, such as 1.5 bar. However, any other predetermined pressure may be used in order break or rupture the compartment divider.

In the following the term "sufficient pressure" may be interpreted to a predetermined pressure based on the design of the bag and compartment divider, sufficient to break or rupture the compartment divider.

Figure 2:
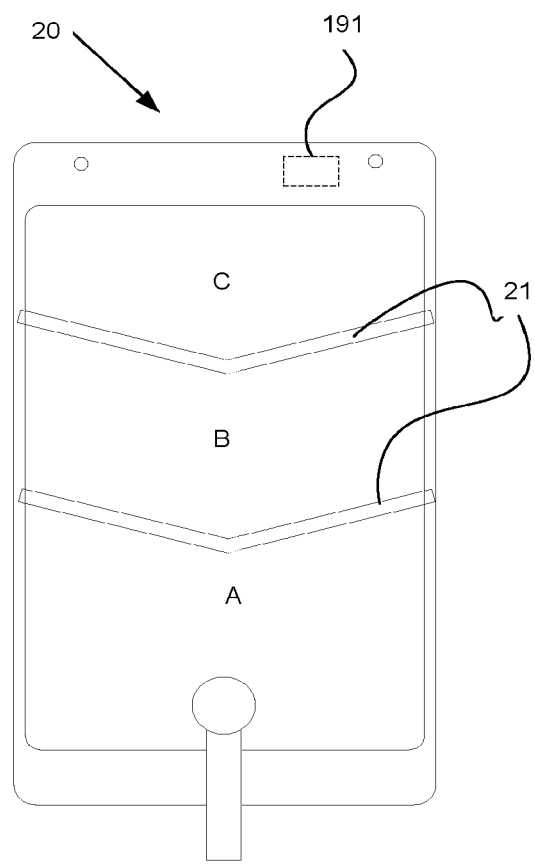

The compartment dividers may be provided in the shape of an arrow tip 21 as illustrated with reference to bag 20 in FIG. 2. The largest tension force exerted on the compartment divider, when fluid is introduced into the bag 20, will be localized at the tip of the arrow shape, and hence, this portion of the compartment divider 21 will open first when increased pressure is applied. The advantage of this embodiment is that the compartment divider opening process, with regard to the location in the bag, is controlled.

Depending on the bag contents and the way of mixing the bag contents, different kinds of compartment divider shapes may be chosen. For instance, a straight compartment divider may be provided as shown in FIG. 1. The compartment divider may have a wave shape. The compartment divider may have a zig-zag shape, which may result in opening of the compartment divider at several locations simultaneously when pressure is applied.

The fluid used for opening the compartment divider may be water provided from a water source. In an embodiment, the water introduced in compartment A may be used for dissolving powder arranged in compartment B, when the compartment divider 6' ruptures. Additional introduction of water will result in that the second compartment divider 6" between compartments B and C ruptures, whereby a solution or a further powder will mix with the contents of the combined compartments A and B, thereby to provide the ready-made medical solution.

In another embodiment, the fluid used to open the compartment divider may be a pressurized gas, such as air or nitrogen gas. In this case, the fluid does not take part in the preparation of the final solution, but is only used for opening the compartment dividers 6' and 6" in order to mix the contents of the compartments. In an embodiment, the lower compartment A comprises water, while the second compartment comprises a power, which dissolves in the solution at mixing. Finally, compartment C may comprise a further powder, which dissolves in the solution at mixing, when the second compartment divider is ruptured.

The nitrogen may also be used to remove free radicals from the oxygen normally contained in the bag.

In an embodiment, the compartment divider is configured to open via chemical reaction or dissolution. The compartment divider may e.g. be closed utilizing a substance, such as non-toxic glue, enabling chemical reaction or dissolution. By introducing a chemical reagent, such as water, into the bag e.g. via the inlet connector, a reaction of the non-toxic glue and the chemical reagent may result in that the glue dissolves and the compartment divider opens.

In an embodiment, the compartment divider is configured to open when the compartment divider is subjected to heating. For example, the compartment divider may be closed using a substance, such as non-toxic heat sensitive glue, enabling thermal dissolution. Hence, by applying heat on the compartment divider, the compartment divider may open.

In an embodiment, the compartment divider may further be a heat conducting material to improve the thermal homogeneity over the compartment divider. For example, a thin metal foil may be used to heat the compartment divider until it opens.

In an embodiment, the compartment divider is configured to open by means of induction. By inducing an electromagnetic field the characteristics of the substance used to close the compartment divider may be altered.

In some embodiments a vacuum chamber is provided, in which the bag according to an embodiment may be inserted. The vacuum chamber may be a part of a bag connection adaptor 160 (mentioned in greater detail below) to which the bag is connected for providing a medical solution. The vacuum chamber may also be used to provide a mixing action of the contents of the bag by successively creating vacuum and letting air into the vacuum chamber. This will result in that the contents of the bag are mixed by being forced out of the bag via a bag connector, such as a bag inlet connector, and into the bag again via the same or other bag connector.

The inlet tube 2 may be remotely connected to a water source providing a metered volume by a water pump. The water to be introduced into the bag should be of medical quality, in order to be compatible with the end product. For a dialysis solution, reversal osmosis water may be used. For solutions to be introduced into the blood circuit, sterile water should be used.

The inlet tube 2 may also be connected to a re-circulation pump providing re-circulation of the contents of the bag.

The water introduced into the bag may be required to be carefully controlled as to the volume thereof. Thus, the water volume is monitored, for example by having a metering pump. The bag may be arranged on a scale, so that the weight of the bag is monitored, and thus, the weight of water introduced into the bag.

The re-circulation pump and the water introduction pump may be a centrifugal pump or a gear pump or a peristaltic pump.

Figure 3:
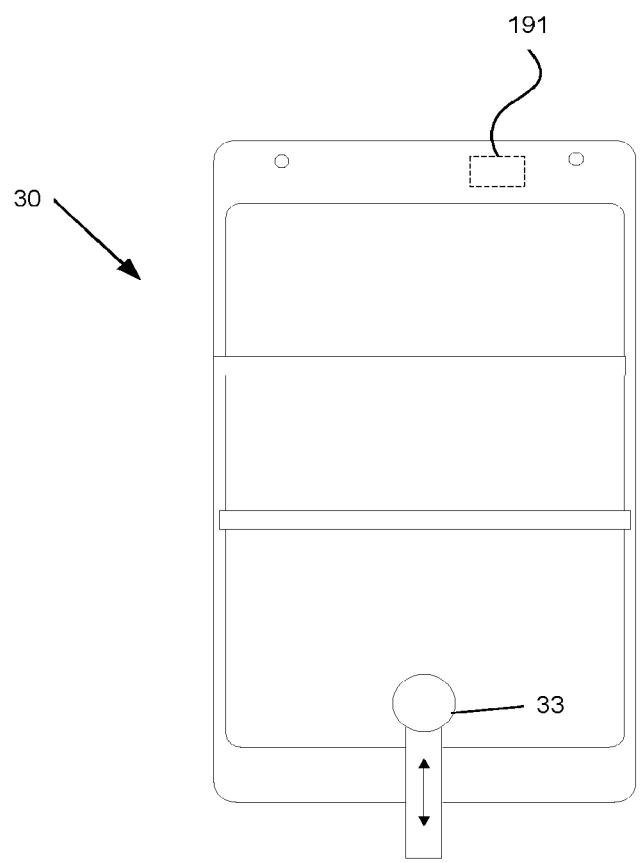

In an embodiment of a bag 30, according to FIG. 3, an inlet connector 33 comprises a valve adapted to enable flow in both directions. A re-circulation pump may be connected to the inlet connector 33 and by alternating the flow of the re-circulation pump back and forth the bag is capable of mixing the contents of the bag. Suitable periods of inflow are combined with suitable periods of backflow providing the mixture. By utilizing a feeding pressure sufficient for opening the compartment divider, controlled mixing of the bag contents of different compartments is obtained.

According to an embodiment of a bag 40, according to FIG. 4, the bag 40, in comparison to the above-described bags 10, 20, 30, further comprises an outlet connector 41 connected to an outlet tube 42. Here, the inlet connector 43 is provided with a check valve, such as a non-return valve, to prevent back flow from the bag into the inlet tube 44. The outlet connector 41 has also a check valve, such as a non-return valve, to prevent back flow from the outlet tube 42 into the bag. By connecting a re-circulation pump (not shown) to the inlet tube 44 and/or outlet tube 42 the bag is capable of mixing water with the contents of the bag by forcing the mixture into the bag via the inlet connector 43 and out of the bag via the outlet connector 41. This re-circulation process provides effective mixing of the contents of the bag with water. The re-circulation process also facilitates the dissolution of a powder in the water, by agitating the water.

In an embodiment of a bag 50, according to FIG. 5 the inlet connector and outlet connector are integrated, as illustrated at 51. The advantage of this embodiment is that only one penetration opening into the bag is required for providing and removing mixture from the bag through two directional access tubes 52, 53, which are provided with non-return valves.

A further embodiment of a bag 60 is illustrated in FIG. 6. The bag 60 is similar to the bag illustrated in FIG. 3, and further comprises an outlet connector 61 located in the upper compartment of the bag 60. The outlet connector 61 has a check valve, such as a non-return valve, to prevent back flow from the outlet tube 62 into the bag. The valve may also be arranged in the outlet tube 62. A re-circulation pump (not shown) connected to the inlet tube 63 performs the mixing of contents of the bag 60 by alternately forcing the mixture out of the bag and into the bag via the inlet connector 64. After the mixing has been completed and a mixed solution is obtained, the mixed solution may be provided to a dialysis circuit via the outlet connector 61.

Figure 10:
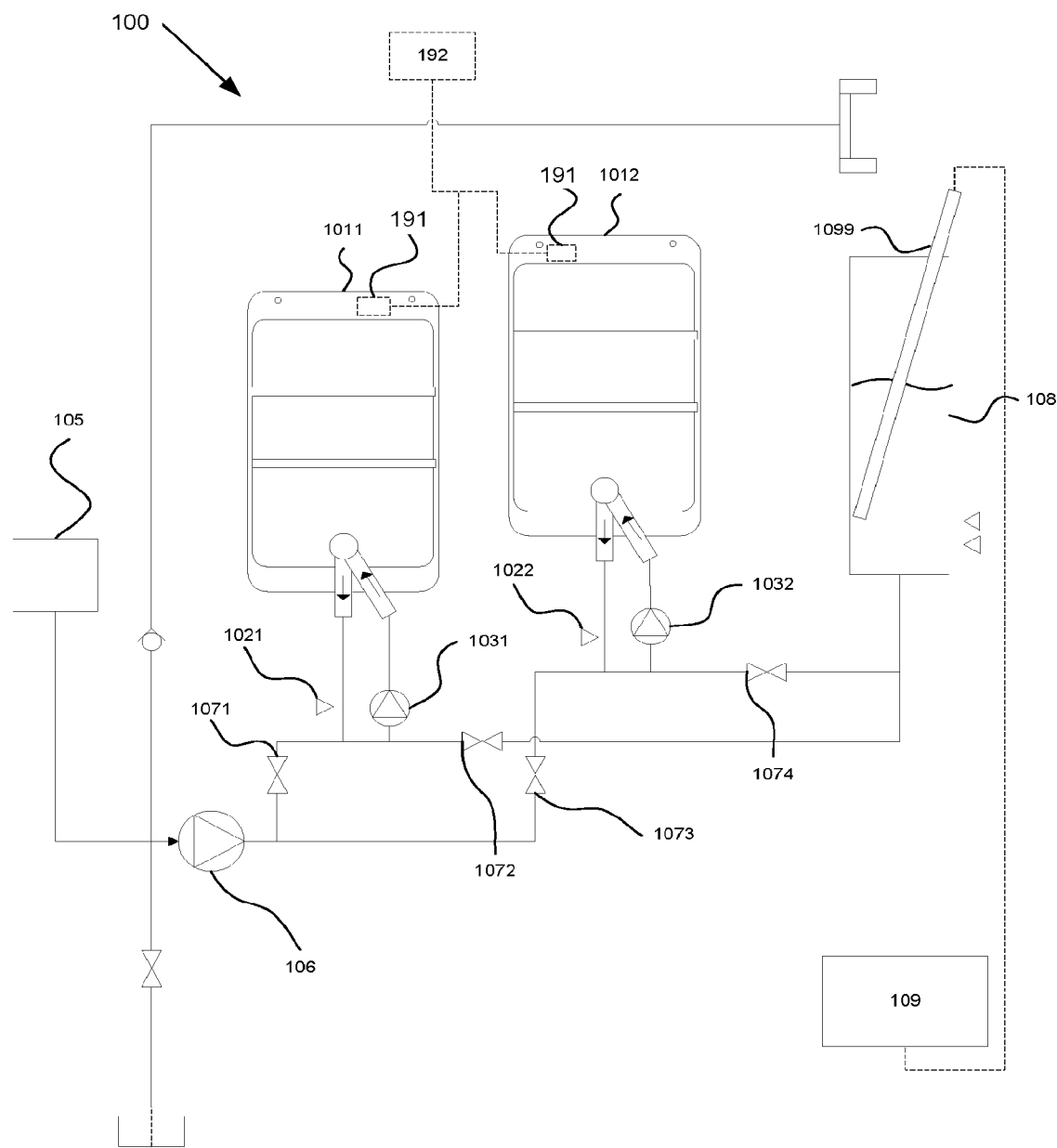

In an embodiment, the outlet connector 61 is configured with a membrane adapted for enabling penetration by means of e.g. a suction tube 1099 connected to a dialysis circuit 109, see FIG. 10. The membrane may be of a flexible plastic material. The membrane may also be made of e.g. aluminum foil or a combination of an aluminum foil and a plastic material, such as polyethene etc.

In an embodiment of a bag 70, according to FIG. 7, the bag illustrated in FIG. 6 further comprises a second outlet connector 71 connected to a second outlet tube 72. The inlet connector 73 has a non-return valve to prevent back flow from the bag into the inlet tube 72. The second outlet connector 71 has also a non-return valve to prevent back flow from the second outlet tube 72 into the bag. By connecting a re-circulation pump (not shown) to the inlet tube 74 and the second outlet tube 72, the bag is capable of mixing water with the contents of the bag by forcing the mixture out of the bag via the second outlet connector 71 and into the bag again via the inlet connector 73. After the mixing has been completed and a mixed solution has been obtained, the mixed solution may be provided to a dialysis circuit via the first outlet connector 75 in the upper compartment of the bag.

Figure 7B:
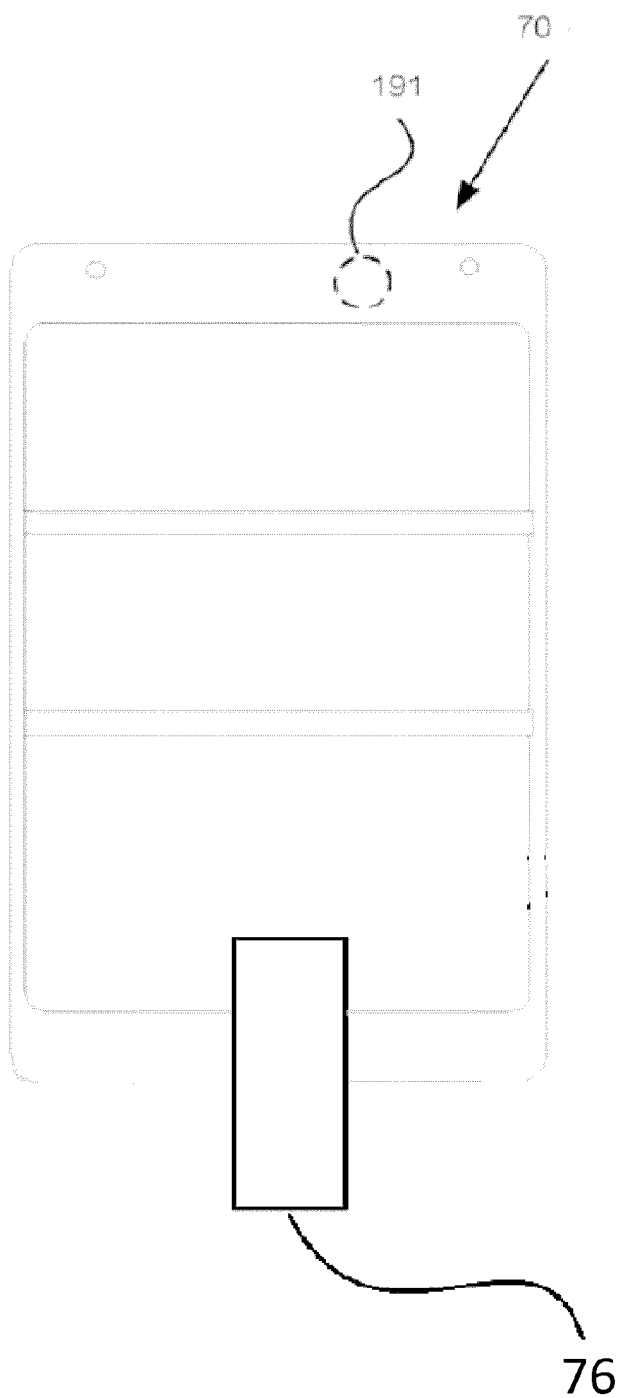

In an embodiment the inlet connector and the second outlet connector of FIG. 7 are integrated (as shown in FIG. 7B). The advantage of this embodiment is that only one penetration opening into the bag is necessary for providing and removing mixture from the bag.

Furthermore, the inlet connector and the outlet connector may be provided as a double lumen connector 76 in FIG. 7B, wherein the inlet connector is a canula provided inside a sleeve that constitutes the outlet connector. Conversely, the outlet connector may be provided as a canula inside the sleeve constituting the inlet connector.

Figure 8:
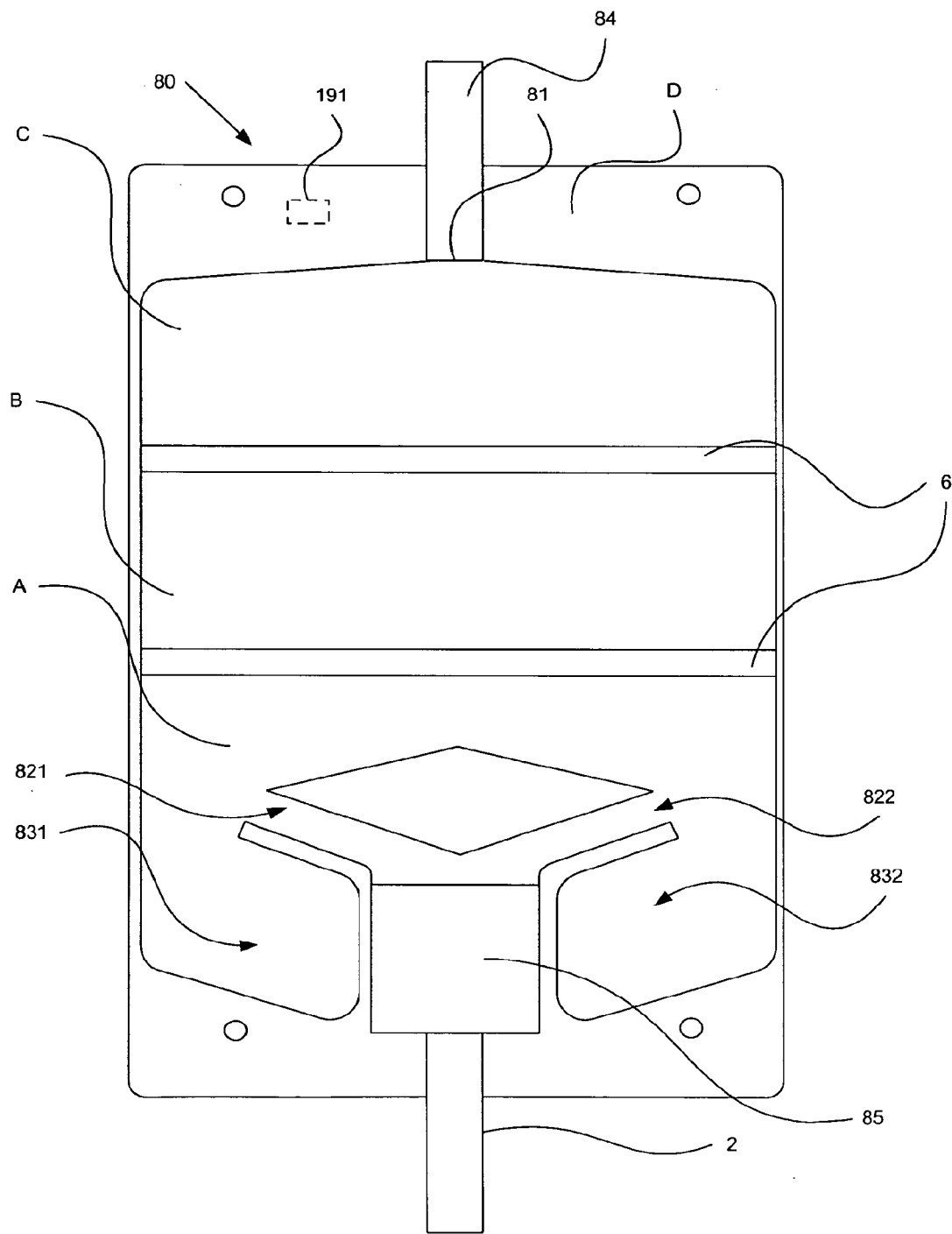

A further embodiment is illustrated in FIG. 8. Here, a bag 80, which is similar to the bag illustrated in FIG. 1, further comprises an outlet connector 81, which is connected to the upper compartment C of the bag. Moreover, the bag 80 comprises two flow distribution channels 821, 822 and two pump compartments 831, 832.

The outlet connector 81 may be equipped with a non-return valve to prevent back flow from the outlet tube 84 into the bag. When water is introduced into the bag by the inlet connector 2, the water is forced through two flow distribution channels 821, 822 and into two pump compartments 831, 832. The pump compartments 831, 832 may be externally pressed, pushed or rolled, in order to provide an internal circulation flow e.g. by means of alternating pistons or similarly functioning mechanisms (not shown). When a mixed solution is obtained, the outlet tube 84 via the outlet connector 81 is capable of transporting the mixed solution e.g. to a dialysis circuit.

The bag 80 of FIG. 8 may be used for providing a sterile dialysis fluid for use in CAPD, HF in batch and HDF in batch. The mixed solution, i.e. dialysis, may in this case either be directly forwarded to a patient's peritoneum (in the CAPD case) via the outlet connector 81 and outlet tube 84 or be stored inside the bag until a treatment is appropriate. The advantage of this embodiment is that a home treatment patient does not have to transport and carry heavy and bulky dialysis fluid containers into his/her home. Instead, by installing a clean water source, and connecting the water source to the bag according to FIG. 8, the treatment is facilitated, as is the burden on the patient.

The bags described herein may be manufactured from a flexible material, such as PVC or PP, providing a leak tight bag. A bio compatible or medical grade material may be used for the bag. The material may suitably be chosen for providing as little interaction of the bag material with the contents thereof as possible. In some embodiments the flexible material comprises at least partly polyethene, polyamide, polypropene, or PET. In some embodiments a combination of different flexible materials may be used. In an embodiment the flexible material comprises an outer PET layer with a thickness of approximately 120 µm to prevent humidity from entering the bag, a middle polyamide layer with a thickness of approximately 15 µm to make the bag durable towards tearing, and an inner polyethene layer with a thickness of approximately 12 µm for enabling welding of the bag.

According to an embodiment the non-return valve of the inlet connector and/or outlet connector may comprise a two-welded thin flat folio design.

The non-return valve in the inlet connector and outlet connector may be any non-return valve, such as a non-return valve with a sliding ball mechanism.

In an embodiment, the bag may be provided with any number n of compartments and thus n−1 compartment dividers, such as two compartments and one compartment divider.

Hence, a bag with one compartment divider may be provided, wherein the upper compartment is filled with powder. An advantage of this embodiment is that the powder cannot disturb the action of a valve mechanism of the connector to the lower compartment.

In an embodiment for providing a solution for CAPD (Continuous Ambulatory Peritoneal Dialysis) or CCPD (Continuous Cycling Peritoneal Dialysis), the compartments of bag 80 may have the following contents:

Compartment A: 2000 ml of water comprising sodium chloride, sodium lactate, calcium chloride, magnesium chloride dissolved in water.

Compartment B: Glucose powder

Compartment C: Additional glucose powder

The bag 80 is activated by the introduction of a gas, such as nitrogen gas in order to rupture the compartment divider 6' between compartments A and B. When the divider 6' ruptures, the glucose powder in compartment B falls into the water solution of compartment A and rapidly dissolves therein. The dissolution of the powder of compartment B is facilitated by pressing the pump areas 831 and 832 in order to agitate the solution. The bag may also be inverted back and forth in order to enable dissolution of all the powder in the compartment B. Thus, a PD solution with a first concentration of glucose is provided, such as 15 gram per liter. If a higher concentration of glucose is desired, such as 25 gram per liter, the gas pressure is further increased in order to rupture the second compartment divider 6". The glucose powder of the third compartment C is then mixed and dissolved in the water contents of the lower compartments A and B. It is noted, that the two compartment dividers 6' and 6" may be opened in a single operation, by keeping a high gas pressure until both dividers have been ruptured.

The entire bag with its contents may be sterile, for example by autoclaving the entire bag 80 with its contents. The introduction of gas into the bag may take place by sterile connectors and the gas may be sterile, so that the final product of medical fluid is sterile.

Other sterile medical fluids may be produced in the same way, such as infusion solutions or replacement solutions.

In an embodiment, the bag is intended for producing a concentrate intended for a dialysis treatment, such as an A-concentrate and a B-concentrate.

A bag 80 for providing an A-concentrate may have the following composition:

Compartment A: Empty, but having a volume of 5 liters. The compartment may be folded in the transport position.

Compartment B: 1050 gram of sodium chloride, 25 gram of potassium chloride, 45 gram of calcium chloride and 34 gram of magnesium chloride all in powder form Compartment C: 200 gram of water comprising 32 gram of acetic acid dissolved in the water.

An A-concentrate for a dialysis treatment is prepared by entering 5 liter of water to compartment A at a pressure so that the compartment divider 6' ruptures. Thus, the powder in compartment B falls down into the water of compartment A and dissolves therein. When all powder has been dissolved, a gas pressure is introduced in order to rupture the second compartment divider 6" so that the acetic acid in compartment C is added to the solution in compartment A and B. This solution should be diluted in a ratio of about 1:34. The water introduced into the compartment A should be compatible with the intended use. RO-water is suitable for the preparation of an A-concentrate. The connectors do not need to be sterile, but should be sufficiently disinfected.

A bag 80 for providing a B-concentrate may have the following composition:

Compartment A: Empty, but having a volume of 9.5 liters. The compartment may be folded in the transport position.

Compartment B: 750 gram of sodium bicarbonate in powder form.

A B-concentrate for a dialysis treatment is prepared by introducing water, such as RO-water, into the compartment A, by means of disinfected connectors. Water is introduced until the compartment divider between compartment A and B ruptures, which should be after introduction of about 9.5 liters of water. Then, additionally 0.5 liters of water is introduced so that all together 10 liters of water are present in the bag. The bicarbonate powder will start to dissolve in the water. The dissolution may be facilitated by agitating the bag, as described above. When all the powder has been dissolved, a ready-made B-concentrate has been obtained which should be diluted in a ratio of about 1:20.

The inlet connector and/or the outlet connector may have a suitable design preventing leakage, such as an interlocking function.

In an embodiment, the bag has the capacity to be completely emptied and thus results in a minimum of waste and minimum weight. It is also much less storage consuming than the commonly used non-flexible plastic containers.

If the contents of a bag are not fully used during treatment, it can be used at the next treatment.

In an embodiment the bag is made from a biodegradable material, such as a biodegradable polymer.

In an embodiment the compartment divider is a weld, which breaks when applying the sufficient pressure value.

According to an embodiment, the compartment divider may be a zip-lock.

In another embodiment the compartment divider is glued or similarly attached.

In an embodiment the compartment divider is provided by an externally attached clip closing the bag.

In an embodiment, the bag is provided with a protecting film such as a semi-transparent or non-transparent film or a protection bag (not shown) protecting the contents of the bag from e.g. sunlight, humidity, heating etc. The protecting film may be provided on the outside of the bag 10 or be integrated in the bag wall. The protection bag may also be provided externally enclosing the bag 10 or may the bag and the protection bag be comprised as an integrated bag. An advantage of this embodiment is that the contents of the bag 10 do not degenerate to the same degree as when no protecting film or protecting bag is provided.

In an embodiment, the interior bottom surface of the bag is inclining towards a lowest point of the bag, when the bag is in an upright position.

In an embodiment, the inlet connector 3 is provided at the location of the lowest point.

In an embodiment, the inclined bottom surface of the bag is further configured with two additional inclined opposing surfaces, being perpendicularly arranged with reference to the inclined bottom surface. The function of the two additional inclined opposing surfaces is to direct the contents of the bag to the lowest point of the bag, and to provide improved mixing of the contents of the bag, as the risk that contents of the bag will remain at the interior walls and in the interior edges of the bag is reduced. By providing the inlet connector 3 at the lowest point and adjacent to the junction of the three inclined surfaces the bag is configured to significantly increase the mixing efficiency as compared when no inclined surface is provided in the bag.

In an embodiment, the bag 10 is adapted to stand without any support when a fluid has been introduced into the bag, which is enabled by providing the walls with a partly rigid plastic material. Accordingly, a fluid filled bag according to this embodiment can be placed onto a planar surface, such as a table or a floor before use.

In an embodiment, the compartment divider is integrated as a part of the inlet connector (not shown) or as a cap provided on the inlet connector. Hence, there may be no compartment divider inside the very bag, and accordingly the bag will only comprise a single compartment. This embodiment is advantageous when there is only one powder in the bag, such as the B-concentrate bag mentioned above.

Recently, a new type of powder has been developed, wherein electrolytes are integrated into a powder of e.g. sodium chloride. Accordingly, in this embodiment it will not be necessary to have a separate electrolyte solution compartment and a separate sodium chloride-powder compartment, but only one compartment comprising the combination powder. This powder may e.g. be obtained from Tomita Pharmaceutical Corp. Ltd. Hence, according to this embodiment the definition of the expression "inlet connector" may be interpreted as an inlet connector provided either with or without a cap or integrated compartment divider.

Figure 9:
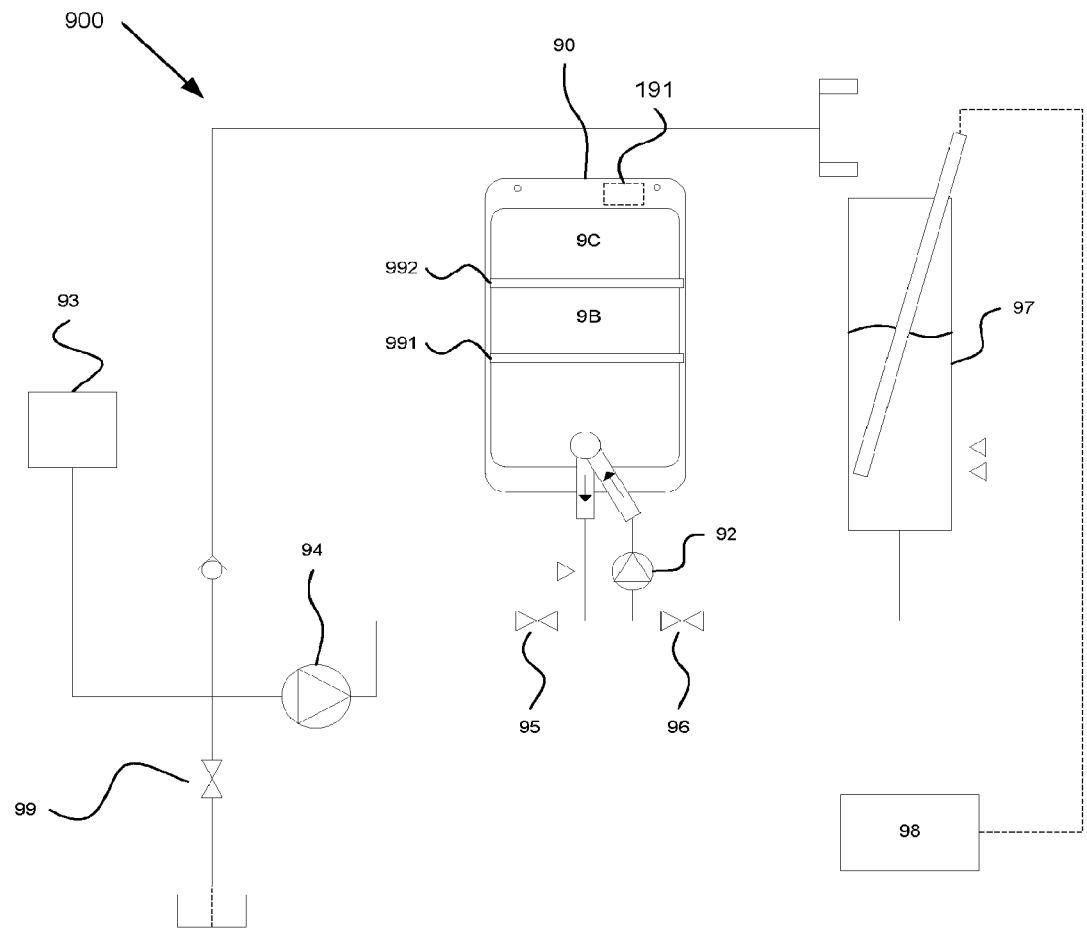
FIGS. 9 to 13 are schematic illustrations of systems according to various embodiments.

In an embodiment, according to FIG. 9, a system 900 is provided. The system comprises a bag 90, as illustrated in FIG. 5, a re-circulation pump 92, a water source 93, a water pump 94, a first valve 95, which is normally opened, a second valve 96, which is normally closed, as well as a solution supply reservoir 97, such as a dialysis batch container. The system may optionally be connected to a circuit 98, such as a dialysis circuit.

The function of the system is to provide a mixed solution to the solution supply reservoir 97 by mixing contents of the different compartments of the bag 90 with water from the water source 93. The bag is capable of being connected to the system, wherein the bag 90 comprises e.g. one compartment 9B containing NaCl powder and one compartment 9C containing concentrated electrolyte solution, while compartment 9A is empty. Water, such as RO-water, is introduced into the bag from the water source 93 via the water pump 94 and via the first valve 95, as valve 96 initially is closed. When a sufficient water volume has been introduced into bag 90, and when the water pressure inside the accessible part of bag 90 has reached the above mentioned first predetermined pressure value, the first compartment divider 991 opens and the NaCl powder is mixed with the introduced water and dissolved therein. At the same time as the compartment divider opens, the water pump 94 is shut off and hence no additional water is introduced into the bag 90, giving a defined volume of water mixed with NaCl powder. Valve 95 is then closed. Alternatively, the water pump continues to introduce water also after the time when the first compartment divider has opened, in order to introduce the predetermined volume of water.

Subsequently, re-circulation pump 92 is initiated to pump the mixture of water and NaCl powder, recirculating it into the bag via the inlet tube and out of the bag via the outlet tube of the bag. The re-circulation pump 92 is active during a first time period until the NaCl powder is completely dissolved in the water. The outlet tube may be provided with a filter preventing particles of the NaCl powder from passing out of the bag, since such particles may disturb the pumping action.

The re-circulation pump 92 may then be stopped and the water pump 94 starts pumping in additional water into the bag 90, by re-opening valve 95. When a sufficient additional water volume has been introduced into bag 90 and when the water pressure has reached a second predetermined pressure value, the second compartment divider 992 opens and the electrolyte solution in compartment 9C is mixed with the NaCl solution already prepared. When the second compartment divider 992 opens, the water pump 94 is shut off again, valve 95 is closed, and the re-circulation pump 92 starts recirculating the mixture out of the bag via the outlet tube and into the bag via the inlet tube.

When the electrolytes are completely mixed with the NaCl solution, the second valve 96 is opened, whereby the solution flows to the solution supply reservoir 97 by gravity.

In an embodiment, the re-circulation pump is capable of pumping the resulting, blended solution out of the bag 90 and into the solution supply reservoir 97. The advantages of this embodiment comprise among others, that the used bag may be replaced by a new bag without stopping the treatment process, as there is continuously sufficient remaining solution in the solution supply reservoir for the treatment. As an example, when there is approximately 10 min of resulting solution left in the bag and the solution supply reservoir 97, before the solution supply reservoir is empty, the recirculation pump pumps the remaining resulting solution out of the bag 90 and into the solution supply reservoir. If more resulting solution is required for the treatment process, a new bag is connected. The disposal of time for preparation of the new bag is thus 10 min. The remaining volume may be determined by a level sensor for determining the remaining level in solution supply reservoir 97 (see 131 in FIG. 13 below), or alternatively by a scale giving the weight of the bag and its remaining contents.

In an embodiment, the water pump is running continuously until the correct, or a sufficient amount of water has been delivered to the bag, independently of when the compartment dividers break. This is for instance implemented by filling the bag in predetermined sufficient time intervals from a defined water source delivering a known flow of water. Alternatively, water flow or pressure measuring sensors may be suitably integrated into the system.

In an embodiment, the recirculation pump 92 is running continuously during a sufficient time interval, such as 5 min., as e.g. empirical studies can be used that have shown that the mixture is ready.

In an embodiment, the system only comprises a single pump, having both water pump capability and recirculation pump capability.

In an embodiment, according to FIG. 10, a system 100 is provided. The system comprises two bags, a first bag 1011 and a second bag 1012 each having the same contents, of the same type as illustrated in FIG. 2, respectively, a first re-circulation pump 1031, a second re-circulation pump 1032, water source 105, a water pump 106, a first valve 1071 normally opened, a second valve 1072 normally closed, a third valve 1073 normally opened, a fourth valve 1074 normally closed, a solution supply reservoir 108, such as a dialysis batch container. The system may optionally be connected to a circuit 109, such as a dialysis circuit, e.g. via a suction tube 1099. The system functions in the same manner as the system in FIG. 9 for each sub-system comprising bag, pump and valves described with reference to FIG. 9. However, implementing two bags in the system allows for filling the second bag 1012 when the first bag 1011 for instance is nearly empty. When the first bag 1011 is completely empty an air detector 1021 will give a signal to automatically change to the second bag 1012. The first bag 1011 may then be exchanged with a new one. The second bag 1012 is also equipped with an air detector 1022. By repeating this cycle there is always enough mixed solution available in the solution supply reservoir 108, thus further improving usable operation time of system 100.

The embodiment according to FIG. 10 may be used for providing a ready mixed dialysis solution having a composition required for dialysis treatment. In this embodiment, bag 1011 comprises components for producing an A-concentrate and bag 1012 comprises components for producing a B-concentrate. After activation of the bags as described above, and after mixing and dissolution of the powders in the compartments, the bags comprise concentrates having a carefully controlled composition. By operating pumps 1031 and 1032, which are metering pumps, for example peristaltic pumps or piston pumps, and by operating the pump 106 to provide RO-water, the contents of the supply reservoir may be controlled to include a dialysis solution having a composition suitable to be delivered to a dialyser without further dilution.

Figure 11:
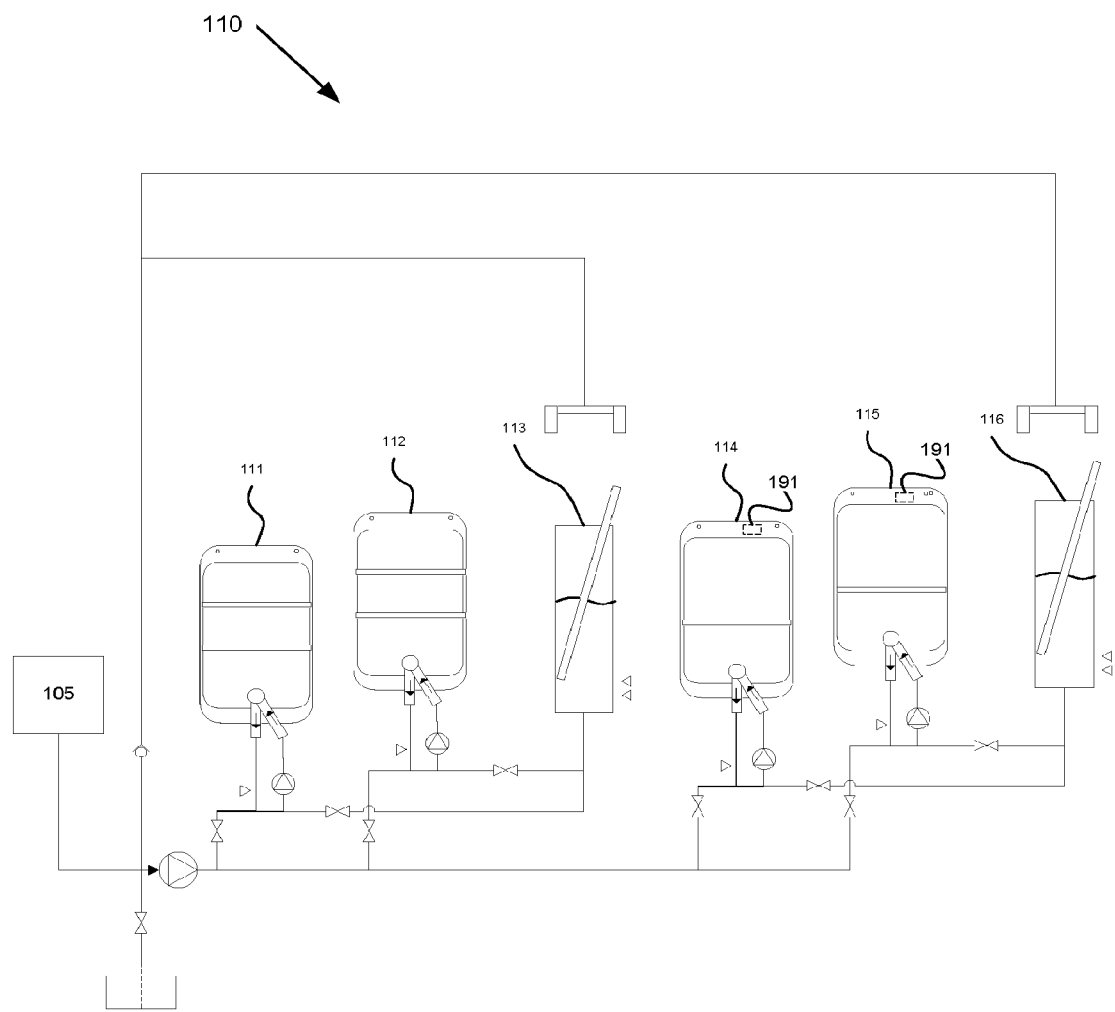

In a further embodiment, according to FIG. 11, a system 110 is provided comprising four bags 111, 112, 114, 115 and two solution supply reservoirs 113, 116. The first bag 111 and second bag 112 are connected to the first solution supply reservoir 113. The third bag 114 and fourth bag 115 are connected to the second solution supply reservoir 116. This system makes it possible to obtain both A-concentrate, e.g. in the sub-system connected to solution supply reservoir 113, and B-concentrate, e.g. in the sub-system connected to solution supply reservoir 116, for dialysis treatment. The reservoirs 113 and 115 are then connected to inlets for the respective concentrates of a conventional dialysis machine.

Figure 12:
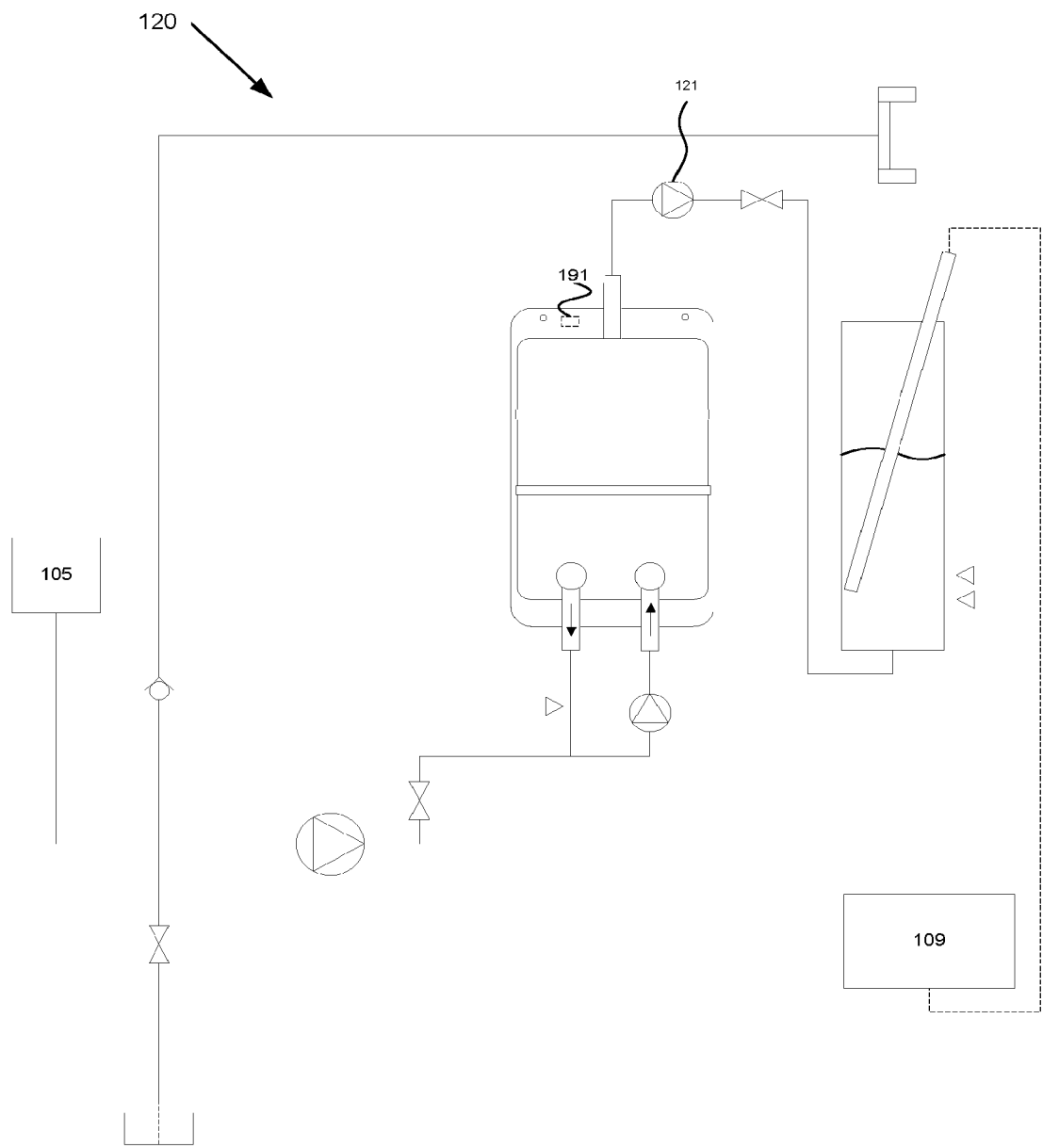

In an embodiment, according to FIG. 12, a system 120 is provided. The system comprises a bag as illustrated in FIG. 7. A pump 121 is capable of pumping resulting solution into the solution supply reservoir.

Figure 13:
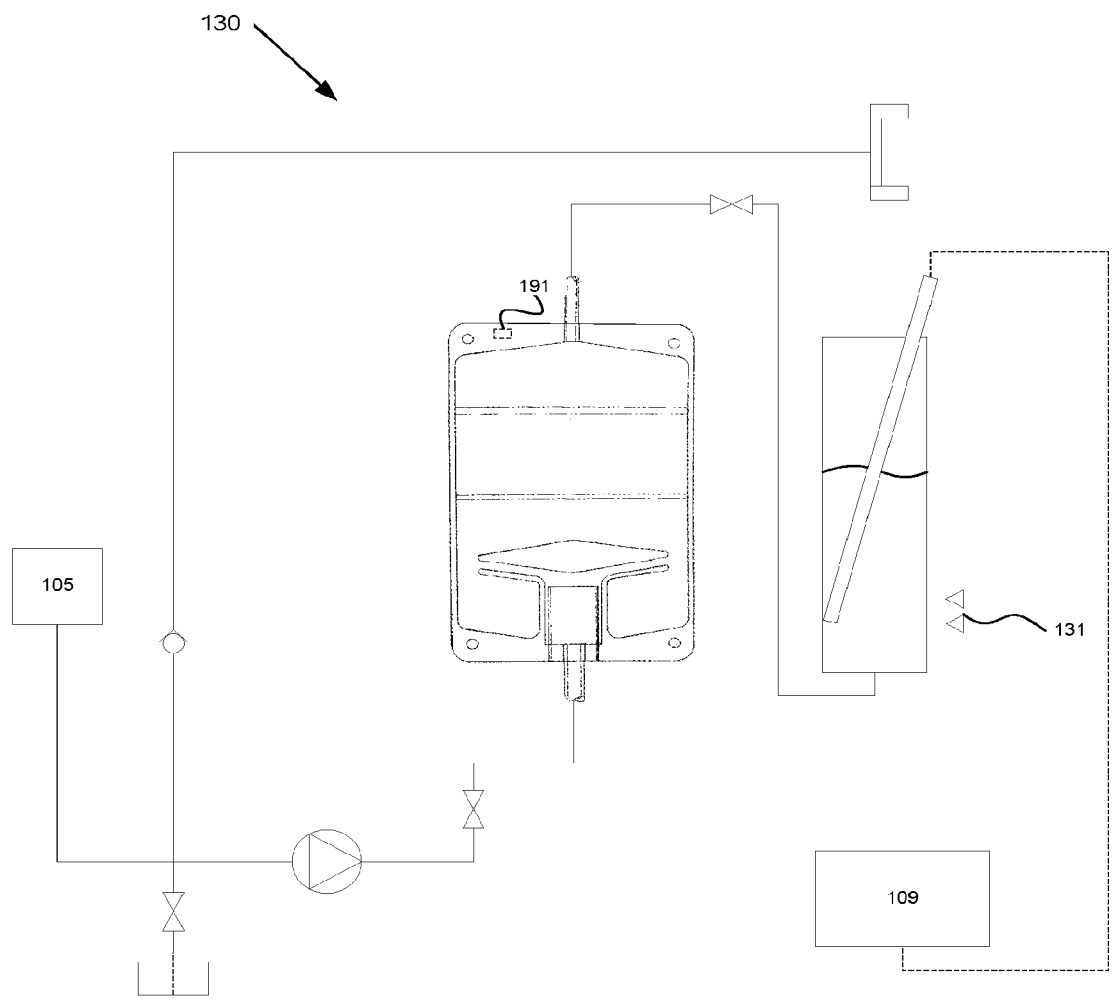

In an embodiment, according to FIG. 13, a system 130 is provided. The system comprises a bag as illustrated in FIG. 8.

According to an embodiment, the solution supply reservoir may additionally have a level sensor 131, see FIG. 13, that alerts the user, e.g. via an external device, when the solution level is too low in the solution supply reservoir and hence a new bag must be connected to the system.

In an embodiment, the level sensor 131 provides information regarding the estimated time left before the solution supply reservoir is empty.

In an embodiment, the level sensor information is presented on a display.

External information, such as urea concentration in the patient, may be presented on the display.

A combination of external information and information from the level sensor is used to calculate the amount of resulting solution required for the treatment, how many bags are required, etc.

In an embodiment the water source is the same water source as is connected to the dialysis circuit, such as a reverse osmosis plant. In another embodiment, the water source is sterile water obtained from bags comprising sterile water.

In an embodiment, the system is used as stand-alone equipment and added to an existing dialysis machine and therefore connected to an existing dialysis system. The system may be connected to the same water source as the dialysis system, e.g. via a T-connection. Furthermore, the solution supply reservoir may be connected to the dialysis circuit. Since the invention is self-supporting, it does not require any rebuilding of existing dialysis machines.

In an embodiment the water pump is a piston pump.

In another embodiment of the present invention the water pump is a gear pump. A gear pump may be used due to economical reasons.

System Emptying Process

Figure 14:
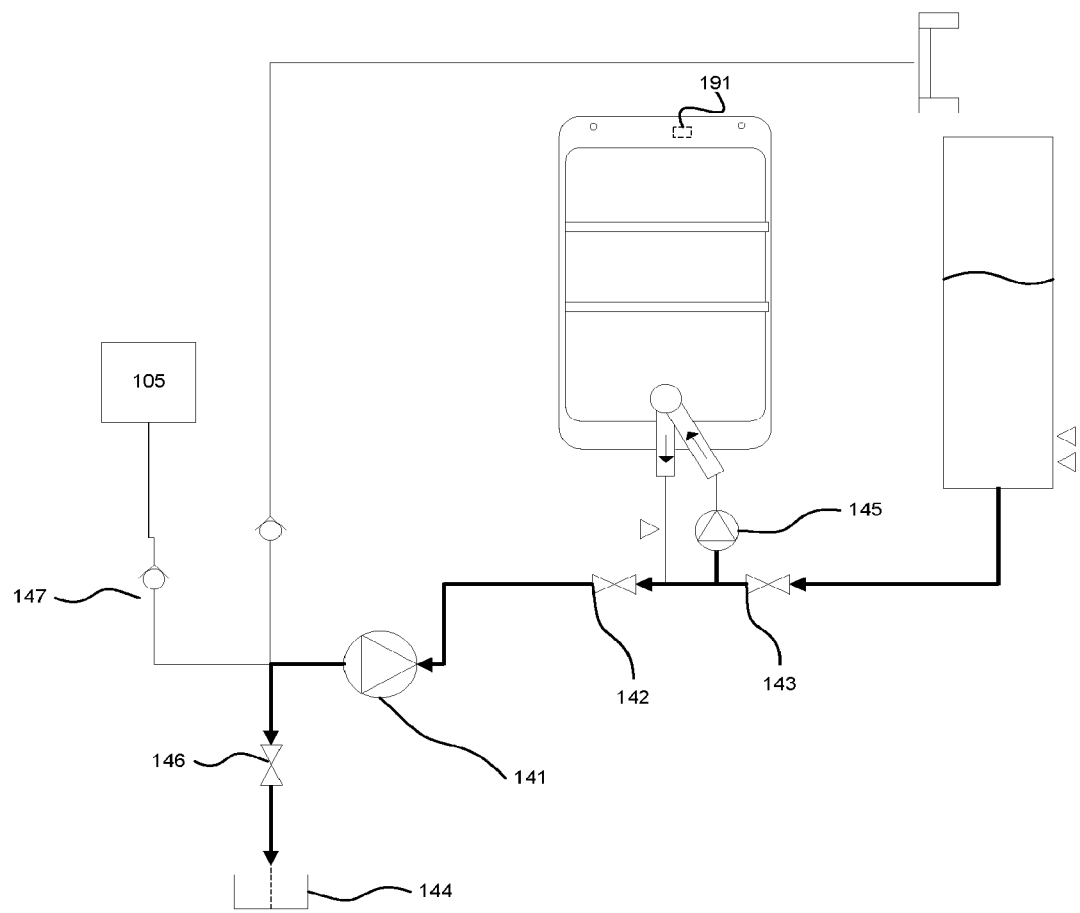
FIG. 14 is an illustration of a system emptying process.

With reference to FIG. 14, a system emptying process is now described. The forward direction flow of the water pump 141, such as a piston pump, is changed into backward direction flow and turned on. The two-way return valves 142, 143 are opened in the direction towards the drain 144. The re-circulation pump 145 is turned on, pumping out the remaining contents of the bag. The system is thus emptied of liquid. A drain valve 146 may be provided to provide communication with drain 144. A non-return valve 147 may be arranged in the line connecting the water source 105 to the pump 141 in order to prevent that liquid be inadvertently pumped into the water source 105.

In an embodiment the pump direction of the re-circulation pump may be changed for facilitating the system emptying process.

Disinfection Process

Figure 15:
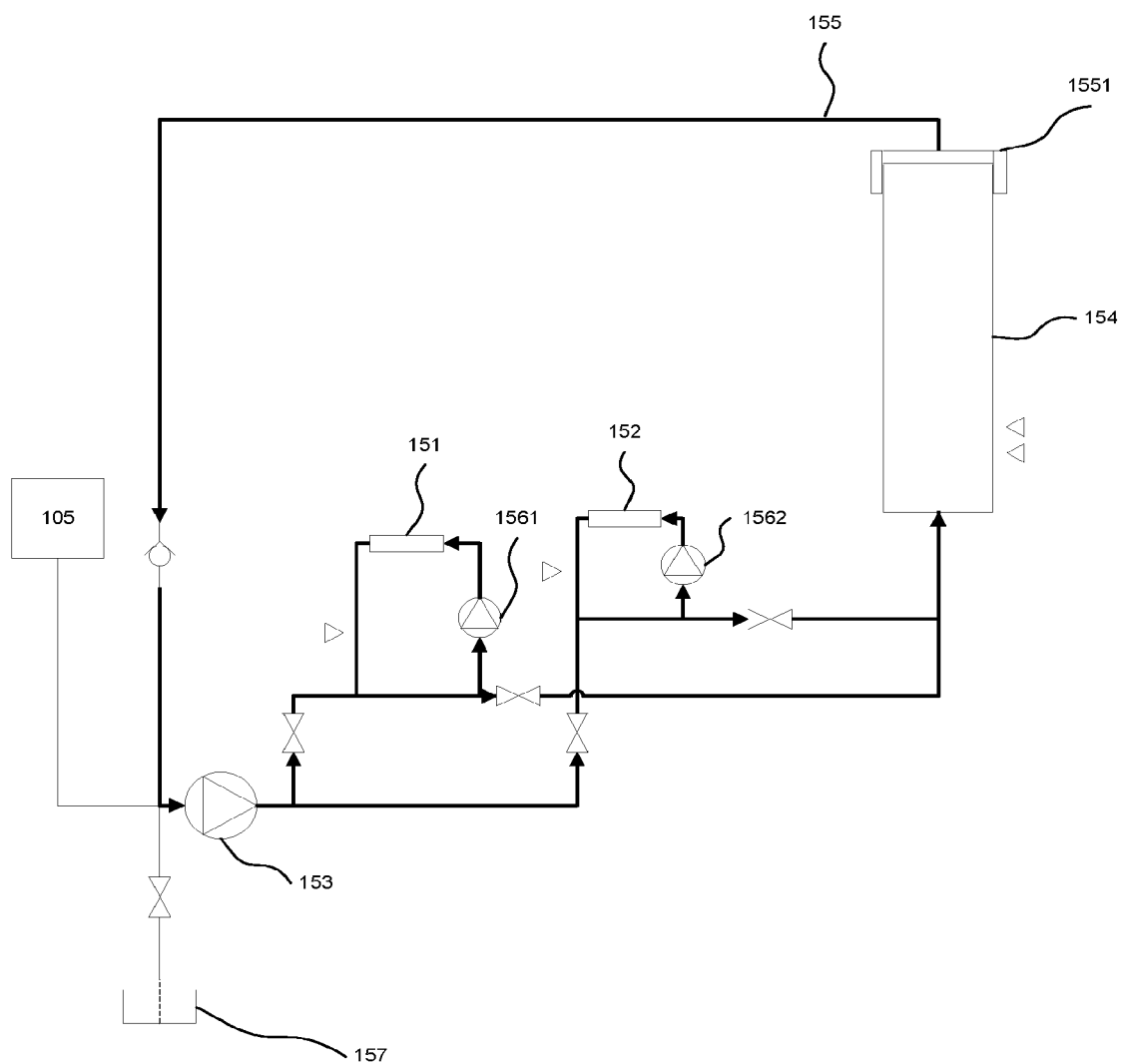
FIG. 15 is an illustration of a system disinfection process.

By referring to FIG. 15, a system disinfection process is described hereinafter. The disinfection process is performed after the above-described system emptying process. The bags are removed and connectors 151, 152 are inserted interconnecting the inlet tubes and outlet tubes previously connected to the bags. The bags themselves may be discarded after single use, and eventually be recycled.

The disinfection process of the system may be summarized in mainly three steps. In the first step, a predetermined volume of clean water is pumped into the system via the water pump 153. All inlet tubes and outlet tubes of the system and the solution supply reservoir 154 are filled with the water. When the water volume has been reached, the water pump 153 is turned off.

In the second step a disinfecting agent (cleaning agent), such as a tablet, powder or liquid, is introduced into the system, e.g. by placing the disinfecting agent in the solution supply reservoir. Alternatively, the disinfecting agent may be placed in the solution supply reservoir before the first step is performed. A disinfection tube 155 is connected to the solution supply reservoir 154, e.g. via a lid 1551. Pump 153 is activated to circulate the disinfecting agent in the system. The re-circulation pumps 1561, 1562 are turned on pumping the water with disinfecting agent around in a re-circulation loop until the disinfecting agent has cleaned the entire system.

In the third step, the system is emptied as explained above and in addition the remaining contents in the disinfection tube 155 is pumped out via the solution supply reservoir 154 and into the drain 157. Additionally, the system may be washed with water to ensure that there is no disinfecting agent residues left in the system before use. The disinfection tube 155 is removed from the solution supply reservoir 154. The system is now disinfected and ready to be used again.

Figures 16A, 16B, 16C:
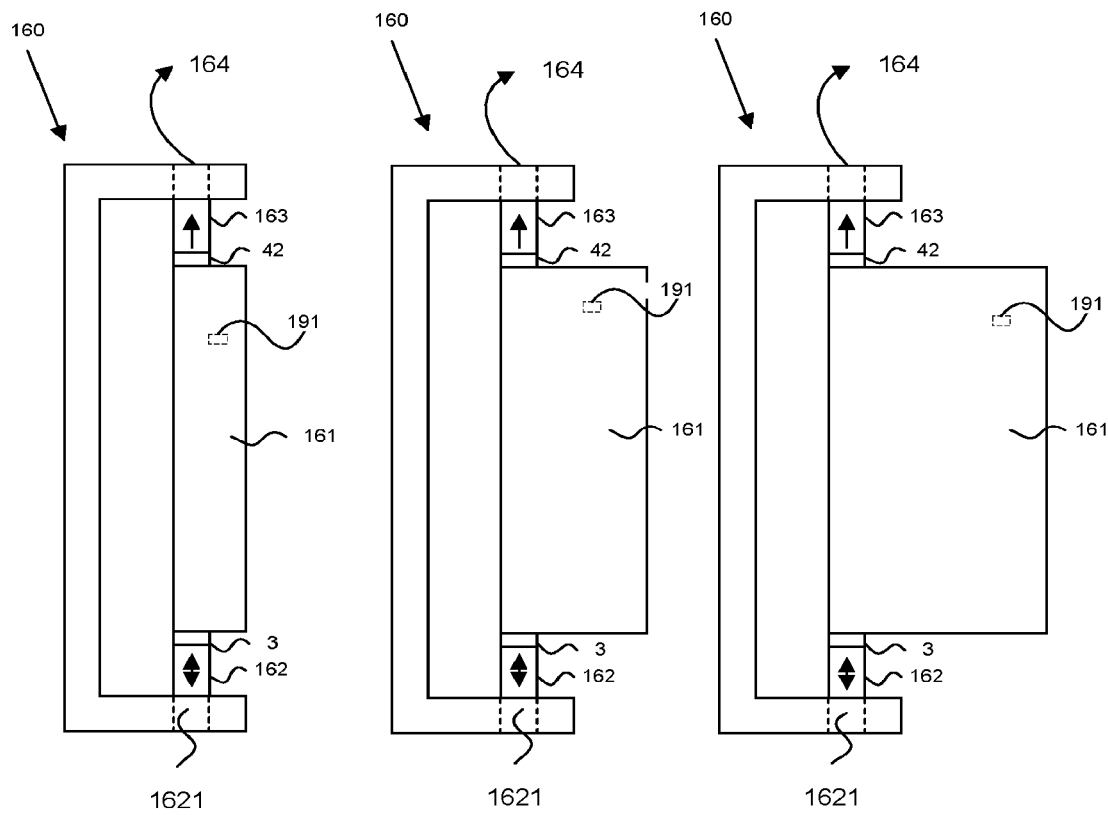
FIGS. 16A-C are illustrations of a bag connection adaptor according to an embodiment.

In an embodiment, according to FIG. 16, the connection of the bag 60, 70, 80, 161 to the system is facilitated by means of a bag connection adaptor 160, being positioned where the bag 161 will be connected to the system. The bag connection adaptor 160 may comprise a first adaptor 162 for connection to the inlet connector 3 of the bag. The first adaptor is at the other end 1621 e.g. connected to the water pump and/or re-circulation pump for enabling filling and mixing of the contents of a connected bag, in accordance with the above described embodiments. In some embodiments, the bag connection adaptor comprises a second adaptor 163 for connection to the outlet connector 33, 61, 75, 81. The second adaptor 163 may also be connected to the outlet connector 42, 53, 62, 84 when provided in the bottom portion of the bag. The second adaptor 163 of the bag connection adaptor may be directly connected 164 to a dialysis circuit or to a solution supply reservoir. The first or second adaptor provides for easy connection of the bag to the system. In sterilization mode, a sterilization connector (151, 152) may be provided and connected between the first 162 and second 163 adaptor to enable sterilization of the bag connection adaptor. Accordingly, using this embodiment the connection of the bag to the system if facilitated.

In some embodiments the bag connection adaptor comprises means for opening the compartment divider of the connected bag. For example, when the compartment divider opens via induction, the bag connection adaptor may comprise means for providing an electromagnetic field enabling opening of the compartment divider. The bag connection adaptor may furthermore comprise a heating means for thermally opening the compartment divider, vacuum means such that the compartment divider is opened by means of external applied vacuum e.g. by configuring the bag connection adaptor with a vacuum chamber in which the bag may be placed. Furthermore, when the bag comprises handle means for mechanically opening the compartment divider, the bag connection adaptor may comprise a mechanical means for grabbing and pulling the bag from two opposite sides, in and outwards manner from the bag in order to open the compartment divider.

Figures 17A, 17B:
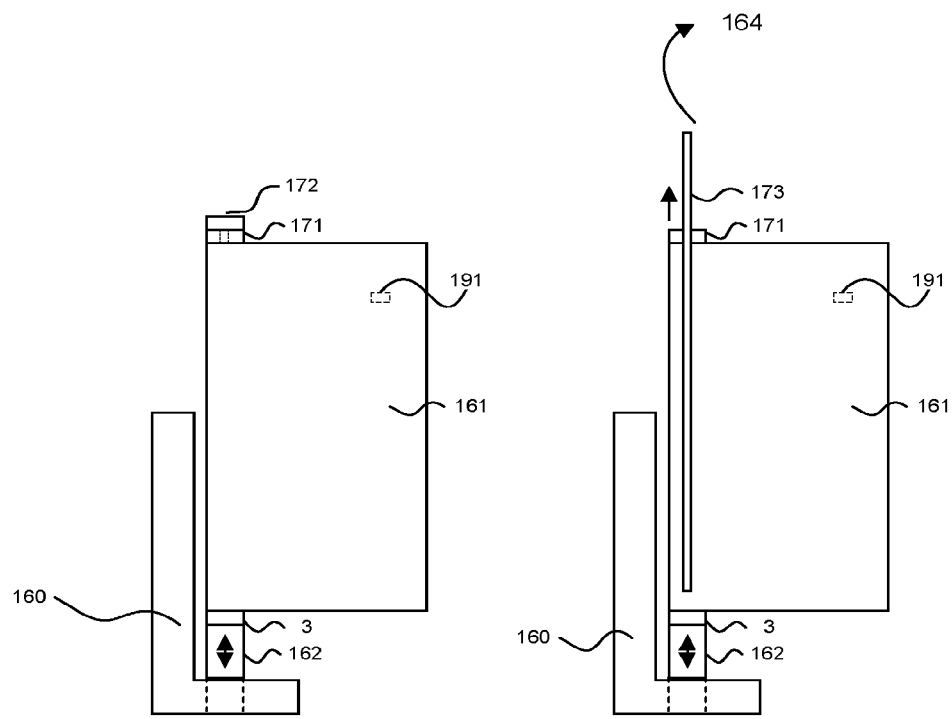
FIGS. 17A-B are illustrations of a container in the form of a bag according to an embodiment.

In an embodiment, according to FIG. 17a and b, the outlet connector 171, e.g. positioned on the top of the bag, is configured with a cap 172, such as a threaded cap. Optionally the bag may be connected to a bag connection adaptor 160 having one connection to the inlet connector 3 of the bag. FIG. 17a illustrates the bag while the cap is still provided on the outlet connector, e.g. during the mixing stage of the contents of the bag. During disinfection of a conventional dialysis machine, a suction tube 173 is placed in a can comprising liquid citric acid via a threaded cap or the like and by suction of an amount of citric acid from the can, the system becomes disinfected. In FIG. 17b the cap has been removed and the suction tube 173 is provided. Disinfection should be performed between each use, to avoid contamination. After disinfection the suction tube(s) are parked in their respective positions in the dialysis system to be part of the disinfection cycle. In this embodiment the outlet connector cap is provided on the bag, and hence the suction tube may be inserted into the bag in a similar way as for the commonly known can with liquid citric acid.

In some embodiments the cap or outlet connector is configured with a thin penetrateable membrane, which may be penetrated by the suction tube. By using a membrane, optional contaminations in the air are kept away from the contents of the bag, as the membrane presses against the outer surface of the suction tube. In this way, the bag according to this embodiment may replace the can comprising liquid citric acid of prior art, improving the flexibility of the way of handling for the user, as no heavy cans of liquid citric acid are needed. Hence, by providing a bag of this embodiment with a citric acid powder, a mixed liquid citric acid solution is provided by means of the mixing action of the bag. In this way, when the disinfection sequence may e.g. be: the powder in the bag is mixed; the cap is opened; the suction tube is placed through the cap opening or through the membrane; the dialysis system draws the amount of liquid citric acid depending on its concentration; the suction tube is removed from the bag; the cap of the bag is closed; after which the dialysis system and the dialysis machine is simultaneously disinfected.

In an embodiment the membrane is injection moulded integrally with the outlet connector. The outlet connector may e.g. have an outer diameter of 16 mm and the membrane diameter accordingly has a diameter corresponding to the inner diameter of the outlet connector. The membrane may be provided with a hole, e.g. with 6 mm in diameter, positioned in the centre of the membrane. The hole is provided to enable the suction tube 171 to be inserted into the bag when the cap has been removed from the bag. Accordingly, the bag according to this embodiment may be used in all existing dialysis systems utilizing a suction tube. FIG. 17 illustrates a bag having a membrane 172 for enabling a suction tube 171 to enter the outlet connector.

There are different ways of controlling the amount of water that is introduced into the bag. The amount of water may be controlled by a volumetric measurement, e.g. by a volumetric pump, by flow measurement, by weight measurement, by conductivity measurement, by pH measurement, by pressure to a flexible bag or by pressure to a bag located in a fixed space. These measurement parameters (volume, flow, weight, pressure, conductivity, pH, pump re-circulation times etc.) are hereinafter referred to as water amount parameters.

According to an embodiment a transponder device 191 is provided on the bag for communicating at least one of the above-mentioned parameters to a control device 192 as exemplified in FIG. 10 within the system and/or to an external device.

The control device and/or external device may communicate information, such as water amount parameters, received from the transponder device to the valves, water pumps, re-circulation pumps, air detectors and level sensors of the system. The control device and/or the external device may optionally communicate by two-way communication. The water amount parameters are individual for each bag design.

In an embodiment, the transponder device communicates water amount information directly to the re-circulation pump regarding re-circulation times, flow rates etc.

In an embodiment, the transponder device communicates water amount information directly to the water pump regarding pump flow, water volume, forward/backward operation etc.

The control device and/or external device may also have the ability to alert by light and/or sound a patient/user of specific conditions, e.g. if the pump settings are not correctly set in reference to the requirements of the bag, the solution supply reservoir is close to empty, if a new bag has to be connected etc.

In an embodiment the control device comprises a display for displaying the parameters such as the remaining treatment time, estimated time until the bag will be empty and hence a new bag may have to be connected, as well as the water amount parameters, ID of the bag etc. In this way a user/patient will have complete general overview of the treatment process.

In an embodiment, the transponder device has a means of identification and a communication interface to communicate this to the control device within the system of the external device.

In an embodiment the outlet connector, when the outlet connector is directly connected to a dialysis circuit, is configured with a flow sensor. Accordingly, the out-flow of mixed solution from the bag may be measured. By knowing the amount of mixed fluid in the bag, the estimated time until the bag will empty may be calculated by the control device. Moreover the flow sensor may be used to calculate the consumption of concentrate, and the remaining amount of concentrate in the bag.

In some embodiments, a flow sensor is provided in an external device, such as a urea sensor, being connected (directly or indirectly) to the outlet connector.

In some embodiments, a flow sensor is provided in the inlet connector for enabling measurement of inlet flow into the bag. The measurement of the inlet flow e.g. enables calculation of estimated time until the bag will be empty.

Another way to determine estimated time until the bag will be empty may be by measuring the liquid column in the bag in conjunction with information of the interior dimension of the bag. In some embodiments, the bag is provided with a volume level indicator along the longitudinal direction of the bag. Accordingly, the volume left in the bag may be observed visually. Optionally, one level scale may be used for each dialysis flow and hence the level meter may comprise several different scales for different outlet flows.

In an embodiment, all bags used in the system have a means of identification. At a dialysis fluid providing system the identification is needed for verifying that a correct bag is attached to the system. The control device within the system or the external device manages the identification codes allowed for a bag to be connected to the system. The means of identification may be labels equipped with bar code or PIN-code, magnetic strip, transponder or chips as means of identification.

Additionally, all valves, water pumps, re-circulation pumps, air detectors and level sensors etc. of the system may have a means of identification.

Additionally, the user/patient may be provided with a means of identification, such as an ID-card with PIN-code, magnetic strip, transponder, data chips etc for the individuals, i.e. patient and operator. In this way the control device and/or the external device may verify that the patient ID corresponds to the bag ID and hence a correct dialysis solution is provided for the user/patient.

The water amount parameters and the means of identification in the system are managed by the control device within the system or by the external device.

In an embodiment, the transponder device on the bag provides both water amount parameters and means of identification to the control device and/or external device.

The control device and/or the external device determine, given the information received from the transponder device, the pressure values, the water volume, time for effective mixing by re-circulation and the additional water volume.

The present embodiments provide many advantages over the prior art. For example, the re-circulation process according to an embodiment of the invention, by using re-circulation pumps, provides an automatic, safe and accurate mixing of the contents of the bag. In the case of treatment by HD, HDF and HF using a bag according to an embodiment, no manual mixing is necessary. Hence, the present invention reduces the risk for the patient/user of doing an error.

By applying water or gas pressure in the bag, opening of the compartment divider is performed automatically. Thus, the user/patient does not need to manually open different compartments of the bag. Hence, the present invention reduces the risk for the patient/user of doing an error.

In A-powder bag providing a solution from powder weighs prior to mixing approximately 1.5 kg. A B-powder bag providing a solution from powder weighs prior to mixing approximately 700 grams. The embodiments can completely substitute liquid concentrate by providing bags with powder that are filled with water at the point of use. Even A-powder bags are provided, since the powder and electrolytes are placed in separate compartments in the bag and mixed firstly at filling with water at the point of use. Thus, it is no longer necessary to use two bags or cartridges for providing an A-concentrate solution.

The bags according to embodiments may be used in any dialysis treatment, such as HD (e.g. for bags 10-70 illustrated in FIG. 1-7) and Peritoneal dialysis (e.g. for the bag 80 shown in FIG. 8) or batch HF and HDF.

The system according to embodiments may be used as a stand-alone device and be added to an existing dialysis machine and therefore be connected to an existing dialysis system just by connecting the system to a water source and connecting the solution supply reservoir to the dialysis fluid inlet of the dialysis system.

Furthermore, the bag according to an embodiment, after use is totally emptied, which accordingly reduces the waste and weight of the used bag.

Moreover, filling and preparation of the bag (FIG. 7) with fluids can be done at separate stations. A home treatment patient may in this way fill several bags and store them until the treatment (PD, CAPD, HF batch or HDF batch) starts.

Although the present invention has been described above with reference to specific embodiments, it is not intended to be limited to the specific form set forth herein. Rather, the invention is limited only by the accompanying claims and other embodiments than the specific above are equally possible within the scope of these appended claims, e.g. different application areas than those described above.

In the claims, the term "comprises/comprising" does not exclude the presence of other elements or steps. Furthermore, although individually listed, a plurality of means, elements or method steps may be implemented. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

What is claimed is:

1. A container for providing a medical solution, comprising:
   at least two compartments, wherein at least one compartment of said two compartments includes a powder; one of said at least two compartments is a lowest compartment configured to receive a volume of liquid;
   an inlet and an outlet integrated into one double lumen connector connected to said lowest compartment;
   a welded compartment divider arranged to separate two of said at least two compartments, said welded compartment divider is configured to break upon said lowest compartment being filled through said inlet with said volume of liquid, and wherein said inlet and said outlet are configured to simultaneously allow an inflow through said inlet and an outflow through said outlet, thereby allowing mixing liquid with said powder by forcing said mixture out of via said outlet and in again via the inlet.

2. The container of claim 1, wherein said compartment divider is provided in the shape of an arrow tip.

3. The container of claim 1, wherein said inlet is provided with a valve.

4. The container of claim 3, where is said valve is a non-return valve.

5. The container of claim 1, wherein said outlet is provided with a valve.

6. The container of claim 5, where is said valve is a non-return valve.

7. The container of claim 1, wherein said inlet is connectable to a liquid pump for supplying said volume of liquid through said inlet.

8. The container of claim 1, wherein said solution includes an electrolyte solution.

9. The container of claim 1, wherein said powder is a bicarbonate powder.

10. The container of claim 1, wherein said outlet is provided with a membrane.

11. The container according to claim 1, further comprising at least one flow distribution channel provided inside a first compartment of the container, wherein each of said flow distribution channels has a proximal end and a distal end, said proximal ends being connected to said inlet and said distal ends being connected to at least one pump compartment, wherein said pump compartments are configured to provide a mixing action in said container by an external alternating press action exerted to said pump compartments.

12. The container of claim 1, wherein said at least two compartments are three compartments, said three compartments are separated by two welded compartment dividers each one of said two welded compartment dividers is breakable upon said lowest compartment being filled through said inlet with a second volume of liquid.

13. The container of claim 12, wherein said lowest compartment is empty and fillable with a liquid.

14. The container of claim 12, wherein said lowest compartment is foldable in a transport position.

15. The container of claim 1, wherein said predefined volume of liquid is at least 5 litres.

16. The container of claim 1, wherein said liquid is water from a source connectable to said inlet.

17. The container of claim 1, wherein at least one of said at least two compartment includes a solution.

18. The container of claim 1, wherein said volume of liquid is a predefined volume of liquid.

19. The container of claim 1, wherein said welded compartment divider is arranged transverse to a longitudinal direction of said container.

20. A system for providing a medical solution, said system comprising:
   a liquid pump configured to be connected to said inlet connector of said container of claim 1, for providing liquid from a liquid source to said container;
   a solution supply reservoir fluidically coupled to said container;
   a re-circulation pump connected to said inlet connector, wherein said re-circulation pump provides re-circulation of the contents of said container with said liquid provided by said liquid pump;
   such that, in use, the medical solution is prepared by mixing contents of said at least one container with said liquid from said liquid source.

21. The system according to claim 20, and further comprising a first valve positioned between said liquid pump and said inlet connector and a second valve positioned between said outlet connector and said solution supply reservoir.

22. The system according to claim 20, wherein said solution supply reservoir is connectable to said container via said outlet connector and comprises a level sensor that alerts a user when a solution level falls below a predetermined value.

23. The system according to claim 20, and further comprising a control device configured to control at least one of said liquid pump, said recirculation pump, a valve based on a liquid amount parameter, an air detector, and level sensor.

24. A method of mixing a solution in a container having at least two compartments wherein at least one compartment includes a powder, comprising:
   providing a volume of liquid through an inlet of a double lumen connector, thereby breaking a welded compartment divider separating two of said at least two compartments;
   mixing said liquid with said powder by simultaneously allowing an outflow through an outlet of said connector and an inflow through said inlet of said connector, thereby mixing said liquid with said powder by forcing said mixture out of said outlet and in again via said inlet.

* * * * *